United States Patent [19]

Nakayama

[11] 3,943,912
[45] Mar. 16, 1976

[54] MEDICAL TREATMENT APPARATUS

[76] Inventor: Takeo Nakayama, 11-19, 5-chome Minamisenju, Arakawa, Tokyo, Japan

[22] Filed: Dec. 12, 1973

[21] Appl. No.: 423,891

[52] U.S. Cl. .................................................. 128/1.3
[51] Int. Cl.² ........................................... A61N 1/42
[58] Field of Search ............ 128/1.3, 1.5, 384, 385, 128/410, 411, 362, 82.1, 380, DIG. 15

[56] References Cited
UNITED STATES PATENTS

| | | | |
|---|---|---|---|
| 198,008 | 11/1877 | Edard | 128/1.3 |
| 237,939 | 2/1881 | Wilson | 128/1.3 |
| 503,811 | 8/1893 | Stephenson et al. | 128/385 |
| 658,027 | 9/1900 | Steiger | 128/1.3 |
| 1,720,002 | 7/1929 | Reynolds | 128/384 |
| 2,597,601 | 5/1952 | Sherman | 128/1.3 |
| 3,480,012 | 11/1969 | Smithers et al. | 128/DIG. 15 |

FOREIGN PATENTS OR APPLICATIONS

| | | | |
|---|---|---|---|
| 1,900,744 | 8/1970 | Germany | 128/1.3 |
| 371 | 1/1879 | United Kingdom | 128/1.3 |
| 259,271 | 5/1965 | Australia | 128/1.3 |
| 1,541,165 | 9/1967 | France | 128/384 |

Primary Examiner—Robert W. Michell
Assistant Examiner—Lee S. Cohen
Attorney, Agent, or Firm—Irving M. Weiner; Pamela S. Burt

[57] ABSTRACT

A belly-band having magnetic medical treatment apparatus attached thereto comprising a double layer main body including a rubberized textured outer layer and an inner cloth layer sewed together, first bristle hook pieces at one end and on one side of the main body, similar second bristle hook pieces, and a plurality of rows of magnet assemblies positioned between said outer and inner layers in an intermediate section of the main body between the opposite ends thereof.

6 Claims, 3 Drawing Figures

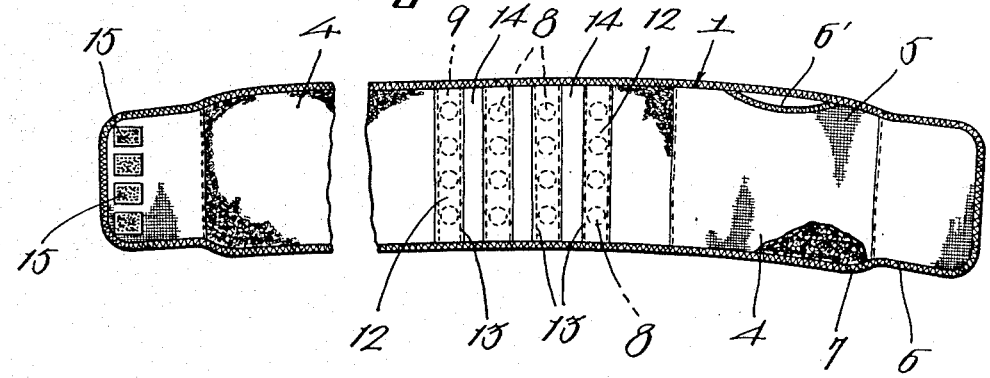

MEDICAL TREATMENT APPARATUS

The present invention relates to a medical treatment apparatus, such as a belly-band to be worn around the belly of a user. In particular, the invention relates to a belly-band having magnetic medical treatment means attached thereto so that the belly-band can serve to protect the user's belly from being chilled and at the same time to magnetically treat any affected part of the user's body.

BACKGROUND OF THE INVENTION

Most of the prior art belly-bands have been formed by knitting woolen yarn or mixture of woolen yarn and rubberized yarns into a ring shape. Some of the prior art belly-bands are formed by a strip of cloth being wound around the belly of a user to protect the belly from being chilled. Furthermore, belly-bands which are particularly adapted to protect a person who rides a horse or motorcycle against gastroptosis have been proposed and employed with certain success and these belly-bands have been formed of a piece of leather having a buckle which secures the opposite ends of the band together. These leather belly-bands can not be used as a general purpose belly-band.

The knitted woolen or combined woolen and rubberized yarn belly-band has an advantage in keeping the belly warm, but such a knitted belly-band can not be satisfactorily held on the belly with the required firmness. In addition, after the knitted belly-band has been repeatedly used, the woolen yarns gradually lose their elasticity. As a result, the belly-band whose woolen yarns have lost their elasticity can not be held in position and frequently and/or invariably slip off the belly. Furthermore, the knitted prior art belly-band would become worn away to the degree that the belly-band can not be used for its expected practical purpose.

Although the belly-band comprising a strip of cloth as referred to above is less expensive as compared with the knitted belly-band, it requires tedious manual work in winding the belly-band around the belly of a person and a skill in obtaining a desired thickness of the band on the belly. That is, when the cloth belly-band is too tightly applied around the belly, the user feels a sense of compression. On the other hand, when the cloth belly-band is too loosely applied around the belly, the band would easily slip off the belly and become useless as the belly-band. The cloth belly-band further has the disadvantage that even if the cloth belly-band has been applied around the belly with a suitable tightness, each time the wearer eats a meal, he must loosen or unwind the belly-band and after the meal, he must rewind the band around the belly with a suitable tightness. In addition, it is difficult to maintain the ends of the cloth belly-band in a stabilized state.

In order to eliminate the disadvantages inherent in the prior art belly-bands referred to above, an improved belly-band has been proposed and the improved belly-band comprised a relatively thin rubberized web main body, a similar configurated relatively thick rubberized main body and having piles on the other side or exposed side, said main body and textured member being sewed together all along their peripheral edges, and a plurality of synthetic resin hook pieces sewed to the other side of the main body and having bristles on the exposed side whereby when the belly-band is applied around the belly of a user, the bristles of the hook pieces interlock with the piles of the textured member. Although the last-mentioned belly-band has successfully eliminated the disadvantages inherent in the knitted woolen yarns, combination of woolen yarns and rubberized yarns, leather and cloth belly-bands, the last-mentioned belly-band which is disclosed in U.S. Pat. No. 3,623,488 is only effective in protecting the user's belly from being chilled or in protecting a motorcycle or horse rider against gastroptosis, but it is ineffective in treating any affected part of the body of a wearer.

SUMMARY OF THE INVENTION

The present invention provides a medical treatment apparatus adapted to be removably secured to a body of the user or to a portion of the body of the user. The apparatus includes a flexible main body, and medical treatment means connected to the flexible main body. The medical treatment means is disposed on the flexible main body to provide at least one predetermined section on the flexible main body between the medical treatment means for receiving at least one bone of the user when the apparatus is secured to the user.

A principal object of the present invention is to provide a novel and improved medical treatment apparatus, such as a belly-band, having magnetic medical treatment means secured thereto which can effectively protect the belly of the wearer from being chilled or against gastroptosis and at the same time, treat any affected part of the wearer's body by the utilization of magnetism obtainable from the magnetic medical treatment means.

Another object of the present invention is to provide a novel and improved belly-band having magnetic medical treatment means attached thereto, in which the magnetic medical treatment means are quite simply and positively attached to the main body of the band.

Another object of the present invention is to provide a novel and improved belly-band having magnetic medical treatment means attached thereto in which the magnetic medical treatment means comprise a plurality of laterally spaced magnet rows each comprising a plurality of vertically spaced magnets are positioned in the intermediate section of the band between the opposite ends thereof with the spacing between adjacent magnet rows corresponding to the position of each of the bones in the back of the wearer and in which first bristle hook pieces are provided at one end of the band on one side thereof and second or mating bristle hook pieces are provided at the other end of the band on the other side thereof for selective interlocking with the first bristle hook pieces to thereby firmly hold the band on the belly of the wearer.

A further object of the present invention is to provide a novel and improved belly-band having magnetic medical treatment means attached thereto in which the magnetic medical treatment means are received in their attachment pieces and are held in position by means of adhesive cellophane tape or strips.

The above and other objects and attendant advantages of the present invention will be more apparant to those skilled in the art from a reading of the following detailed description in conjunction with the accompanying drawing which illustrates one preferred embodiment of a belly-band having magnetic medical treatment means attached thereto constructed in accordance with the present invention for illustrative purpose only, but not limiting the scope of the same in any

BRIEF DESCRIPTION OF THE DRAWINGS

The accompanying drawing shows one preferred embodiment of a belly-band having magnetic medical treatment means attached thereto; in which FIG. 1 is an elevational view of a belly-band, with a portion broken away, of the invention showing the inner or reverse side of the band which directly contacts the belly of a human body when worn on the belly;

FIG. 2 is a fragmentary view of said belly-band on an enlarged scale, with a portion of the innermost cloth layer of the band broken away, to show the novel magnetic medical treatment means of the invention; and FIG. 3 is a cross-sectional view taken substantially along the line A — A of FIG. 2.

DETAILED DESCRIPTION OF A PREFERRED EMBODIMENT OF THE INVENTION

The present invention will now be described referring to the accompanying drawing which shows one preferred embodiment of a medical treatment apparatus, such as a belly-band according to the invention. The belly-band generally comprises a main body 1 in the form of an expansible rubberized web which has such a length and width that, when worn around the belly of a user, the opposite free ends of the band will overlap one upon another and cover the entire belly. The main body 1 includes a substantially constant width intermediate section, and opposite end sections which have a width narrower than that of the intermediate section.

The main body 1 comprises an expansible thicker rubberized textured outer layer 2 to one side or the outer side of which a great number of napping piles 3 are adhered by means of a suitable conventional adhesive, and a thinner inner cloth layer 4 having substantially the same size as the rubberized textured outer layer 2 and sewed to the other side or inner side of the textured outer layer 2 all along the peripheral edges of both the layers. A folded rubberized strip 6 is applied all along 2 and 4, respectively, with the opposite folded portions of the strip 6 embracing the peripheral edges of both the rubberized textured and cloth layers and sewed to the two layers by means of a stitch thread 7 to thereby complete the main body 1. A small piece of cloth 5 is sewn to the side of the cloth layer 4 opposite from the rubberized textured layer 2 adjacent to one end or the right-hand end of the main body 1 (as seen in FIG. 1) and a portion 6' of the top edge of the cloth piece 5 is left unsewed so as to provide a pocket. The unsewed portion of the top edge of the cloth piece 5 is also embraced by a folded rubberized strip sewed thereto.

Medical treatment means including a plurality of small cicular flat magnets 8 are provided in four laterally spaced rows in the intermediate section of the main body 1 between the textured and cloth layers 2 and 4, respectively, and each row includes a plurality of vertically spaced magnets (four magnets in each row in the illustrated embodiment). The magnets 8 in each row are received in the corresponding number of holes 10 formed in its associated attachment piece 9 which has a width greater than the diameter of the magnets 8 and which is held in position by means of an adhesive cellophane strip 11 applied on the side of the magnets 8 opposite from the attachment piece 9 and having a width smaller than the diameter of the magnets 8. A cloth strip 12 is further applied on the cellophane strip 11 and has a width greater than that of the attachment piece 9.

The cloth strips 12 are sewed to the inner side of the cloth layer 4 in the intermediate section of the main body 1 all along their peripheral edges as shown with numeral 13 so as to hold the magnets 8 in position. The attachment pieces 9 have substantially the same thickness as the flat circular magnets 8 and are formed of a foam synthetic resin (or the attachment pieces 9 may be formed of sponge rubber). The lateral spacing or predetermined section 14 between the adjacent vertical magnet rows is so selected that when the belly-band is properly worn on the belly of a user, the bones in the back of the user are positioned in the spacings 14.

A plurality of vertically-spaced hook pieces 15 formed of synthetic bristles are sewed to the inner side of the cloth layer 4 and thus, the inner side of the main body 1 at the end thereof opposite from the end where the cloth piece or pocket 5 is formed. Although not shown, similar mating bristle hook pieces are sewed to the outer side of the main body 1 in a vertically spaced relationship and in a plurality of laterally spaced rows. The bristle hook pieces on the opposite sides of the main body 1 interlock with each other when the user wears the belly-band around his belly so that the belly-band may be held on the belly with a suitable tightness and a comfortable elasticity afforded by the elasticity of the entire belly-band. The provision of the plurality of laterally spaced bristle hook pieces on the outer side of the main body 1 enables the user to select one suitable row of the mating bristle hook pieces out of the plural rows depending upon the peripheral size of his belly.

With the above construction and arrangement of the component parts of the belly-band having magnetic medical treatment means attached thereto constructed in accordance with the present invention, when the user wears the belly-band around his belly so as to position the spacings 14 between the adjacent magnet rows on the bones in the back of his body and then bring the bristle hook pieces 15 at one end of the main body into engagement with one selected row of the mating similar bristle hook pieces at the other end, the main body serves to protect the belly from being chilled, while the magnetism from the magnets penetrates deep into his body to treat the belly and other parts of his body.

And since the magnets are received in the hole in the foam synthetic resin attachment pieces and held in position by the cellophane strips 11 both of which attachment pieces 9 and cellophane strips 11 are sewed to the main body 1 together with the cloth strips 12, the magnets 8 can be firmly held against dislodgment and-/or falling off. Furthermore, the belly-band can be easily worn by a user requiring no tedious procedure and enjoys a relatively prolonged service life. Finally, since the magnets 8 are received in the foam synthetic resin attachment pieces 9, only the area where the magnets 8 are located is hard and the remainder of the band is soft. As a result, the magnets 8 provide a kind of finger-pressure treatment action.

A medical treatment apparatus according to the present invention has been described above with reference to a belly-band. However, various other forms of such apparatus are also contemplated by the invention, e.g., belts, garments, bands, waistcoats, underclothing, and other articles of apparel.

While only one embodiment of the invention has been shown and described in detail it will be understood that the same is for illustration purpose only and not to be taken as a definition of the invention, reference being had for this purpose to the appended claims.

I claim:

1. A magnetic medical treatment belly-band adapted to be removably secured to a body of a user or to a portion of the body of said user and wherein magnetic force is utilized to achieve a desired magnetic flux which is caused to act upon the body of the user, comprising, in combination:

a flexible main body having such a length that when it is worn around a portion of the body of said user, the opposite ends overlap each other;

and wherein said flexible main body includes:

a thick rubberized textured layer;

a thinner piece of cloth having a configuration substantially corresponding to that of said thick rubberized textured layer and sewed to one side of said thick rubberized textured layer;

said piece of cloth having a size smaller than that of said rubberized textured layer with respect to the length and width thereof;

a plurality of bristle hook pieces disposed on the side of said cloth piece opposite from said thick rubberized textured layer at one end of said main body;

a plurality of similar bristle hook pieces disposed on the side of said thick rubberized textured layer opposite from said cloth piece at the other end of said main body for selectively interlocking with said first-mentioned bristle hook pieces;

a pocket provided on said one side of said cloth piece adjacent said other end of said main body;

said flexible main body being provided with a plurality of magnet receiving detachment pieces disposed in laterally spaced rows between said rubberized textured layer and said cloth piece in the intermediate section of said main body between the opposite ends thereof;

and medical treatment means including a plurality of laterally spaced magnet rows interposed between said rubberized textured layer and said cloth piece in the intermediate section of said main body between the opposite ends thereof, said medical treatment means being connected to said flexible main body;

each of said magnet rows includes a plurality of vertically spaced magnets;

each said attachment piece having substantially the same thickness as said magnets and having a plurality of vertically spaced holes each receiving one of said magnets;

an adhesive tape which is connected to the magnets of each magnet row to hold said magnets in position and which is sewed to said one side of said cloth piece; and said medical treatment means being disposed on said flexible main body to provide at least one predetermined section on said flexible main body between adjacent magnetic receiving attachment pieces for receiving at least one bone of said user when said belly-band is secured to said user.

2. A medical treatment apparatus according to claim 1, wherein:

said flexible main body comprises an elongated elastic main body.

3. A medical treatment apparatus according to claim 1, wherein:

each of said magnets is in the form of a circular flat magnet.

4. A medical treatment apparatus according to claim 1, wherein:

said rubberized textured layer is expansible.

5. A medical treatment apparatus according to claim 4, wherein:

said magnet receiving attachment pieces are formed of synthetic resin.

6. A medical treatment apparatus according to claim 1, wherein said magnet receiving attachment pieces are formed of sponge rubber.

* * * * *